US012765819B2

(12) United States Patent
Zhang

(10) Patent No.: US 12,765,819 B2
(45) Date of Patent: Oct. 20, 2026

(54) LANCET DEVICE

(71) Applicant: TIANJIN HUAHONG TECHNOLOGY CO., LTD., Tianjin (CN)

(72) Inventor: Libo Zhang, Tianjin (CN)

(73) Assignee: TIANJIN HUAHONG TECHNOLOGY CO., LTD., Tianjin (CN)

( * ) Notice: Subject to any disclaimer, the term of this patent is extended or adjusted under 35 U.S.C. 154(b) by 682 days.

(21) Appl. No.: 16/872,601

(22) Filed: May 12, 2020

(65) Prior Publication Data

US 2020/0352496 A1 Nov. 12, 2020

(30) Foreign Application Priority Data

May 12, 2019 (CN) ......................... 201910391367.3

(51) Int. Cl.
*A61B 5/151* (2006.01)
*A61B 5/15* (2006.01)

(52) U.S. Cl.
CPC .... *A61B 5/15117* (2013.01); *A61B 5/150572* (2013.01); *A61B 5/15111* (2013.01); *A61B 5/1513* (2013.01); *A61B 5/15144* (2013.01)

(58) Field of Classification Search
CPC .......... A61B 5/15182; A61B 5/150725; A61B 5/150183; A61B 5/15146; A61B 5/150564; A61B 5/15161; A61B 5/15153; A61B 5/150916; A61B 5/150412; A61B 5/150519; A61B 5/15113;

(Continued)

(56) References Cited

U.S. PATENT DOCUMENTS

2014/0379016 A1* 12/2014 Zhang .............. A61B 5/150022 606/182

FOREIGN PATENT DOCUMENTS

CN 100370950 * 2/2008
CN 101431936 * 5/2009

(Continued)

OTHER PUBLICATIONS

Machine Translation of TW-M494592U, Patent Translate, pp. 1-11, printed on Dec. 12, 2022, (Year: 2015).*
Machine Translation of WO-2010050350-A1, Patent Translate, pp. 1-15, printed on Dec. 12, 2022, (Year: 2010).*
Machine Translation of CN-100370950, Patent Translate, pp. 1-13, printed on Dec. 12, 2022, (Year: 2008).*

(Continued)

*Primary Examiner* — Jennifer Robertson
*Assistant Examiner* — Om Patel
(74) *Attorney, Agent, or Firm* — Scully, Scott, Murphy & Presser, P.C.

(57) ABSTRACT

Disclosed is a lancet device including: a body; a head cap, wherein a first end of the head cap is provided with a needle outlet hole, and a second end of the head cap is connected to the first end of the body; a needle seat and a blood taking needle, wherein the needle seat is provided in the body, the blood taking needle is provided to the needle seat, and the needle tip of the blood taking needle is adapted to extend out from the needle outlet hole; a driving core, which is adapted to drive the needle seat to move toward the needle outlet hole; and a driving spring for providing a trigger elastic force for the driving core, wherein: the first end of the needle seat is provided with elastic arms that are evenly distributed in the circumferential direction, and the elastic arms elastically abut against an inner wall of the head cap or an annular wall provided in the head cap.

13 Claims, 8 Drawing Sheets

(58) Field of Classification Search
CPC ........ A61B 5/150618; A61B 5/150022; A61B 5/15–15117; A61B 5/15126–1513; A61B 5/1544; A61B 5/15111; A61B 5/150534–150572
See application file for complete search history.

(56) References Cited

FOREIGN PATENT DOCUMENTS

| | | | | | | |
|---|---|---|---|---|---|---|
| CN | 102188251 | A | | 9/2011 | | |
| CN | 203042258 | U | | 7/2013 | | |
| CN | 203328703 | U | | 12/2013 | | |
| JP | 2004512129 | A | * | 4/2004 | | |
| KR | 20010013343 | | * | 2/2001 | | |
| TW | M494592 | U | * | 2/2015 | | |
| TW | 201513832 | | * | 4/2015 | | |
| WO | WO-0113794 | A1 | * | 3/2001 | ....... | A61B 5/150022 |
| WO | WO-2006118224 | A1 | * | 11/2006 | ........... | A61B 5/1411 |
| WO | WO-2010050350 | A1 | * | 5/2010 | ......... | A61B 5/14532 |

OTHER PUBLICATIONS

Machine Translation of CN-101431936, Patent Translate, pp. 1-16, printed on Dec. 12, 2022, (Year: 2009).*
Machine Translation of WO-2006118224-A1, Patent Translate, pp. 1-24, printed on Dec. 12, 2022, (Year: 2006).*
Machine Translation of KR-20010013343, Patent Translate, pp. 1-17, printed on May 4, 2023 (Year: 2001).*
Machine Translation for JP 2004512129 A, Patent Translate, pp. 1-18, printed on Aug. 21, 2024 (Year: 2004).*
Machine Translation of TW 201513832, Patent Translate, pp. 1-22, printed on Mar. 12, 2026 (Year: 2015).*
Office Action for corresponding Chinese Application No. 201910391367.3, dated Jul. 14, 2022.
Second Office Action and English translation for corresponding Chinese Application No. 201910391367.3, dated Jan. 19, 2023.
Office Action and English translation for corresponding Chinese Application No. 201910391367.3, dated Jun. 29, 2023.

* cited by examiner

LANCET DEVICE

CROSS-REFERENCE TO RELATED PATENT APPLICATIONS

This application claims the benefit of priority of Chinese Patent Application number 201910391367.3 filed May 12, 2019, which is incorporated by reference herein in its entirety.

FIELD OF THE INVENTION

Embodiments of the present disclosure relate to the field of medical devices, and in particular, to a lancet device.

BACKGROUND OF THE INVENTION

A known lancet device includes a lancet device body and a head cap, and a blood taking needle is installed in the lancet device body. The blood taking needle is prone to jitter during the puncture process, which increases the pain of a user.

SUMMARY OF THE INVENTION

In order to alleviate or solve at least one aspect of the above problems, the present disclosure is proposed.

According to one aspect of the embodiments of the present disclosure, the present disclosure provides a lancet device, including:

a body;

a head cap, wherein a first end of the head cap is provided with a needle outlet hole, and a second end of the head cap is connected to the first end of the body;

a needle seat and a blood taking needle, wherein the needle seat is provided in the body, the blood taking needle is provided to the needle seat, and the needle tip of the blood taking needle is adapted to extend out from the needle outlet hole;

a driving core, which is adapted to drive the needle seat to move toward the needle outlet hole; and a driving spring for providing a trigger elastic force for the driving core, wherein:

the first end of the needle seat is provided with elastic arms that are evenly distributed in the circumferential direction, and the elastic arms elastically abut against an inner wall of the head cap or an annular wall provided in the head cap.

According to another aspect of the embodiments of the present disclosure, the present disclosure provides a lancet device, including:

a body, having a first end and a second end;

a head cap, wherein the first end of the head cap is provided with a needle outlet hole, and the second end of the head cap is connected to the first end of the body;

a tail cap, wherein the first end of the tail cap is connected to the second end of the body;

a needle core assembly, at least a part of which is axially guided and located in the body, wherein the needle core assembly includes a needle seat and a blood taking needle, the blood taking needle is provided to the needle seat, and the needle tip of the blood taking needle is adapted to extend out from the needle outlet hole;

a trigger assembly, having a driving core acting on the needle seat, wherein the driving core is adapted to drive the needle seat to move toward the needle outlet hole based on a trigger operation; and a driving spring for providing a trigger elastic force for the driving core, wherein, the first end of the needle seat is provided with elastic arms that are evenly distributed in the circumferential direction, and the elastic arms elastically abut against an inner wall of the head cap or an annular wall provided in the head cap.

BRIEF DESCRIPTION OF THE DRAWINGS

FIG. 2-1 to FIG. 2-4 are schematic diagrams of a needle seat of a lancet device according to an exemplary embodiment of the present disclosure;

FIG. 3-1 to FIG. 3-2 are schematic diagrams of a stop block of a lancet device according to an exemplary embodiment of the present disclosure;

FIG. 4-1 to FIG. 4-4 are schematic diagrams of a guide sleeve of a lancet device according to an exemplary embodiment of the present disclosure;

FIG. 6-1 to FIG. 6-4 are schematic diagrams of a cylinder of a lancet device according to an exemplary embodiment of the present disclosure;

FIG. 7-1 to FIG. 7-2 are schematic diagrams of a button of a lancet device according to an exemplary embodiment of the present disclosure;

FIG. 8-1 to FIG. 8-4 are schematic diagrams of a tail cap core of a lancet device according to an exemplary embodiment of the present disclosure;

FIG. 10-1 to FIG. 10-3 are schematic diagrams of a tail cap housing of a lancet device according to an exemplary embodiment of the present disclosure;

FIG. 12-1 to FIG. 12-3 are schematic diagrams of a second blocking piece of a lancet device according to an exemplary embodiment of the present disclosure;

FIG. 14-1 to FIG. 14-2 are sectional views of a lancet device in maximum and minimum states of puncture distance and elastic force according to an exemplary embodiment of the present disclosure when a driving spring is in a free state;

FIG. 15-1 to FIG. 15-2 are sectional views of a lancet device in maximum and minimum states of puncture distance and elastic force according to an exemplary embodiment of the present disclosure when a driving spring is in a pre-pressed state;

FIG. 16-1 to FIG. 16-2 are sectional views of a needle tip puncture distance in maximum and minimum states of puncture distance and elastic force of a lancet device according to an exemplary embodiment of the present disclosure;

DETAILED DESCRIPTION OF THE EMBODIMENTS

Figures 1, 2:
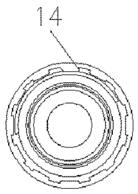
FIG. 1-1 to FIG. 1-4 are schematic diagrams of a cap of a lancet device according to an exemplary embodiment of the present disclosure.
Figure 1:
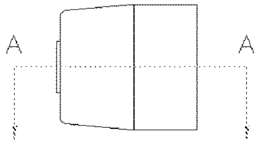
Figures 1, 2, 3:
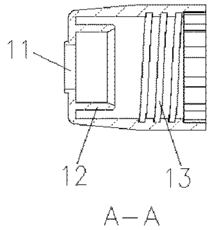

The technical solutions of the present disclosure are further described in detail below through the embodiments and the drawings. In the description, the same or similar reference signs indicate the same or similar components. The following description of the embodiments of the present disclosure with reference to the drawings is intended to explain the general inventive concept of the present disclosure, and should not be construed as a limitation of the present disclosure.

The structure and installation of a lancet device according to an exemplary embodiment of the present disclosure are described below with reference to the drawings. It should be pointed out that, for the clarity of display, some features or components in some drawings are not specifically shown.

A needle seat 20 is provided with a needle seat groove 21 in the direction of a needle outlet hole to accommodate and fix a blood taking needle 50 (referring to FIG. 14-1 and FIG. 14-2); and the needle seat groove 21 is provided with a plurality of elastic pieces 23 on the periphery (referring to FIG. 2-4), and the maximum outer diameter of an outer side wall of the elastic piece 23 is slightly greater than the inner diameter of a limiting rib 12 (referring to FIG. 1-3 and FIG. 14-1 and FIG. 14-2). During a blood collection process, the needle seat 20 moves back and forth in a cap 10 axially, and the needle seat 20 moves smoothly via the deformation of the elastic pieces 23, thereby reducing the jitter of the blood taking needle during the blood collection process and reducing the pain of the user.

A guide rib 27 is installed in a guide sleeve 40 along a first guide groove 48 (referring to FIG. 4-2), until a second matching surface 28 is in contact with a front end face 41.

A column 33 of a stop block 30 is installed along a through hole 25 in a state that a first catching piece 34 is caught by a first matching surface 26, and a second catching piece 35 is caught by a notch 24.

The guide sleeve 40 in which the needle seat 20 and the stop block 30 are installed is installed in a housing 60, a button 70 has been placed in the housing 60 in advance, a trigger surface 72 is exposed to the outside of the housing 60 through a button hole 63, an edge 71 is retained in the housing 60, and a contact point 73 is close to a needle outlet hole 11; a first hook 43 is retained on the same side as the button hole 63, and an assembling groove 44 is installed along a mounting rib 61, until a first positioning surface 45 abuts against a front end face 66.

A cap 10 is an internally hollow housing and is provided to the guide sleeve 40 in a sleeving manner, a first thread groove 13 is screwed onto a first thread rib 42, the cap 10 can move along the axial direction in a departing manner or an approaching manner through the cooperation of the first thread groove 13 and the first thread rib 42; when a bottom surface 15 abuts against a second positioning surface 49 (referring to FIG. 4-1), the cap 10 is located at the nearest end, at this time, the puncture depth of the blood taking needle is the maximum, and when the first hook 43 at the farthest end acts on a blocking surface 14, the puncture depth of the blood taking needle is the minimum. One end of the cap 10 is provided with the needle outlet hole 11, so that the blood taking needle can be installed in the body and can perform the puncturing; a circle of limiting rib 12 (forming an annular wall, and the annular wall can also be an intermittent structure in the circumferential direction) is provided around the needle outlet hole 11, and the space formed between the limiting rib 12 and the housing of the cap 10 can accommodate a part of a spring 140 so as to limit the amount of circumferential swing of the spring 140 (referring to FIG. 14-1 and FIG. 14-2).

Figures 1, 2, 3, 4:
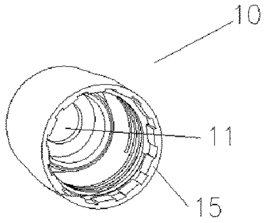
Figures 1, 2:
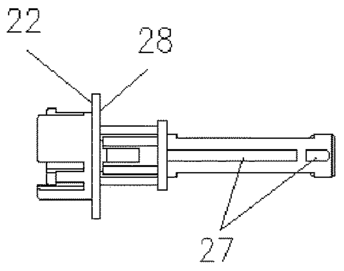
Figures 2, 3:
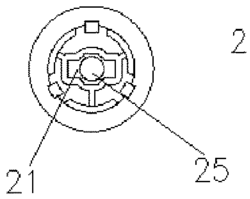
Figures 2, 3, 4:
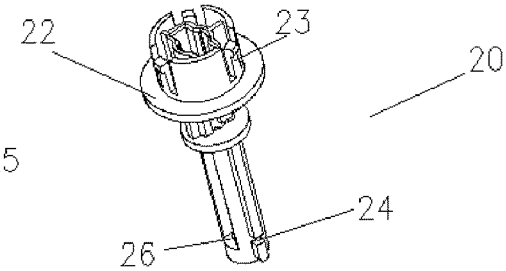
Figure 2:
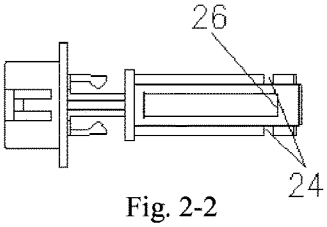
Figures 1, 3:
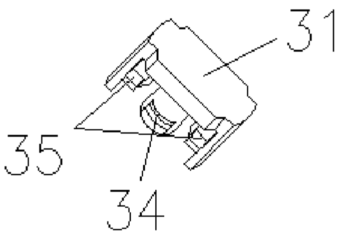
Figures 2, 3:
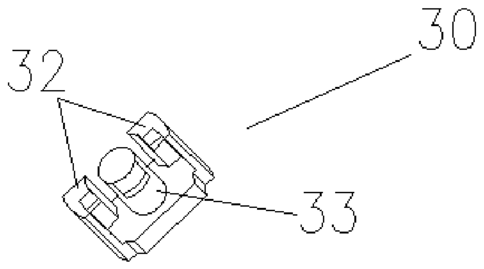
Figures 2, 4:
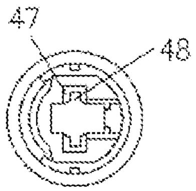
Figures 1, 4:
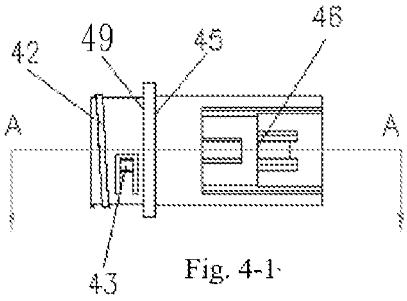
Figure 4:
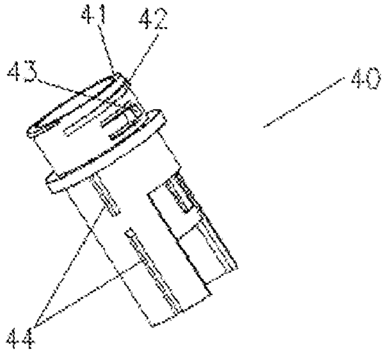
Figures 3, 4:
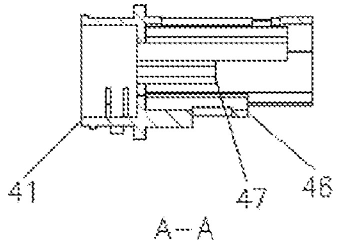
Figure 5:
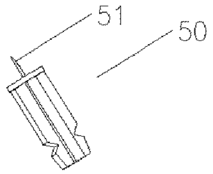
FIG. 5 is a schematic diagram of a blood taking needle of a lancet device according to an exemplary embodiment of the present disclosure.
Figures 2, 6:
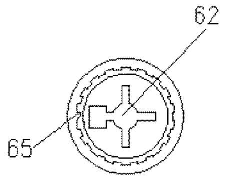
Figures 1, 6:
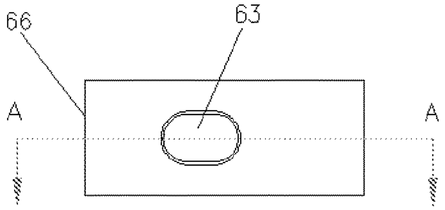
Figures 4, 6:
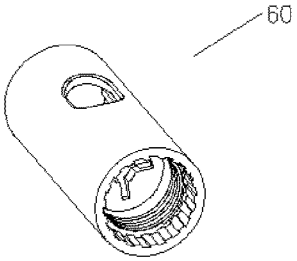
Figures 3, 6:
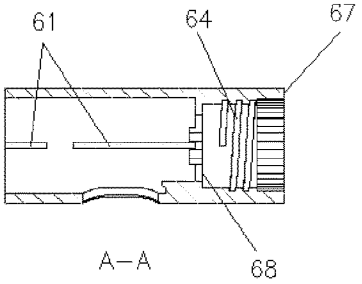
Figures 1, 7:
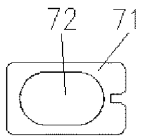
Figures 2, 7:
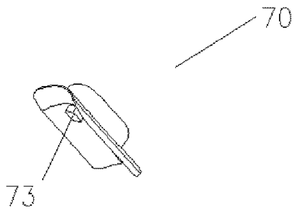
Figures 1, 8:
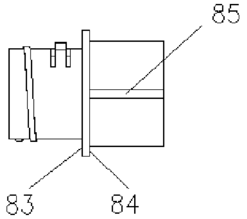
Figures 2, 8:
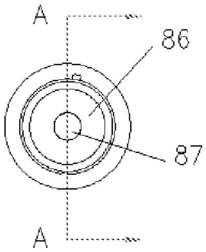
Figures 3, 8:
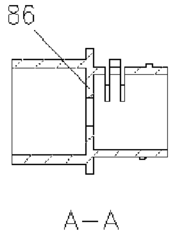
Figures 4, 8:
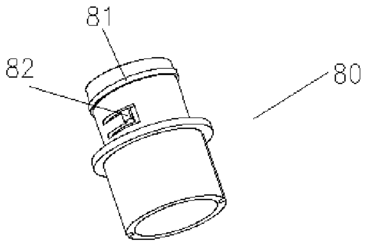
Figure 9:
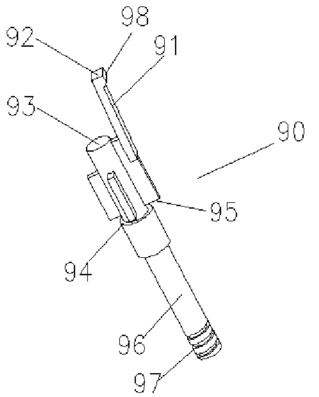
FIG. 9 is a schematic diagram of a driving core of a lancet device according to an exemplary embodiment of the present disclosure.
Figures 1, 10:
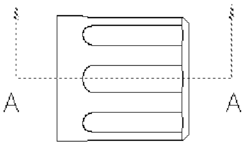
Figures 2, 10:
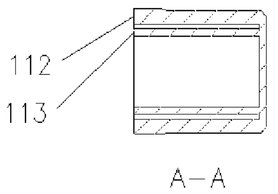
Figures 3, 10:
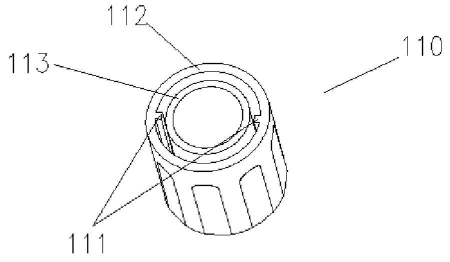
Figure 11:
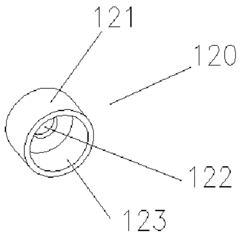
FIG. 11 is a schematic diagram of a first blocking piece of a lancet device according to an exemplary embodiment of the present disclosure.
Figures 1, 12:
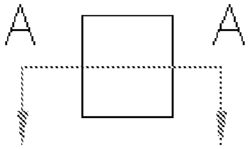
Figures 2, 12:
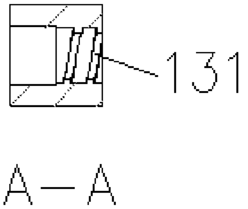
Figures 3, 12:
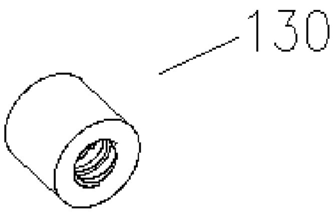
Figure 13:
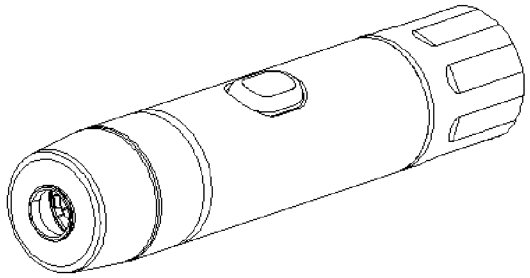
FIG. 13 is a three-dimensional schematic diagram of a lancet device according to an exemplary embodiment of the present disclosure.
Figures 1, 14:
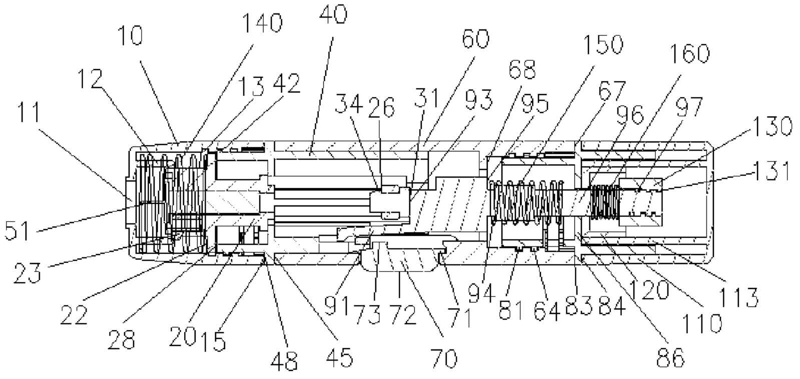
Figures 2, 14:
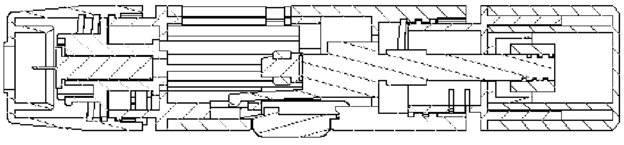

A spring 150 is provided to a column 96 of a driving core 90 in a sleeving manner (referring to FIG. 14-1 and FIG. 14-2), and then the column 96 is installed into a tail cap core 80 in a direction of facing a second thread rib 81, the tail cap core 80 is divided into two parts by a separation piece 86, a first through hole 87 is formed in the middle of the separation piece for the passage of the column 96; then, a first blocking piece 120 is provided to the column in the sleeving manner, and an opening 123 of the first blocking 120 faces toward a second thread groove 97 of the driving core 90; the first blocking piece 120 is a cylindrical housing provided with a second through hole 122 at one end, the outer diameter of the first blocking piece 120 is greater than that of the first through hole 87, so that the first blocking piece 120 is blocked by the separation piece 86, and then a spring 160 is provided to the column 96 in the sleeving manner (referring to FIG. 14-1 and FIG. 14-2); and a second blocking piece 130 is a cylinder provided with a through hole therein, a part of the through hole is provided with a third thread 131, the part without the thread of the second blocking piece 130 faces toward the spring 160, the third thread 131 is screwed to the second thread groove 97, and the spring 160 can be arranged between the first blocking piece 120 and the second blocking piece 130 (referring to FIG. 14-1 and FIG. 14-2).

A tail cap 110 is a housing provided with an opening at one end, the tail cap includes therein a circle of rib 113, the inner diameter of the rib 113 is less than the outer diameter of the first blocking piece 120, so that the first blocking piece 120 is in interference fit with the rib 113, the foregoing inner core assembly is installed from the opening of the tail cap 110, and a second guide groove 85 is aligned with a positioning rib 111, until an end face 112 is in contact with a fourth positioning surface 84. The driving core 90 of this component passes through a second through hole 62 (referring to FIG. 19, FIG. 6-1 to FIG. 6-4, and FIG. 9), an elastic arm 91 is aligned with a button hole 63, and the second thread rib 81 is in screw connection with a second thread groove 64 of the foregoing main body assembly, until a third positioning surface 83 abuts against a rear end face 67 (referring to FIG. 14-1 and FIG. 14-2). The entire lancet device is assembled.

The operation of the lancet device according to the exemplary embodiment of the present disclosure will be described below with reference to the drawings. It should be pointed out that, for the clarity of display, some features or components in some drawings are not specifically shown.

Figures 1, 15:
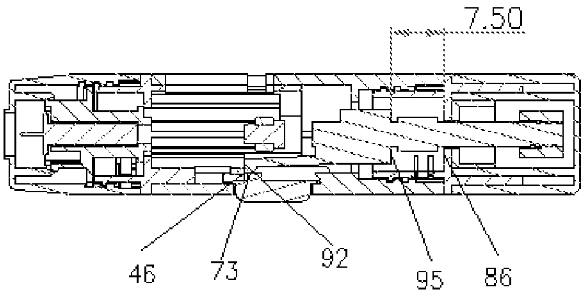
Figures 2, 15:
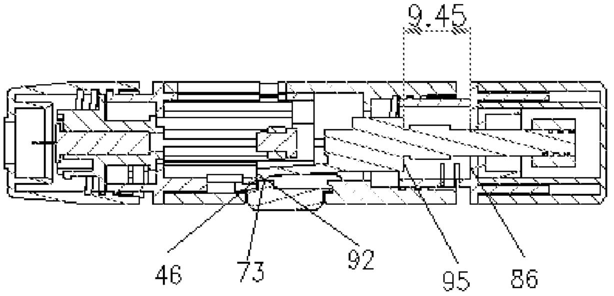
Figure 17:
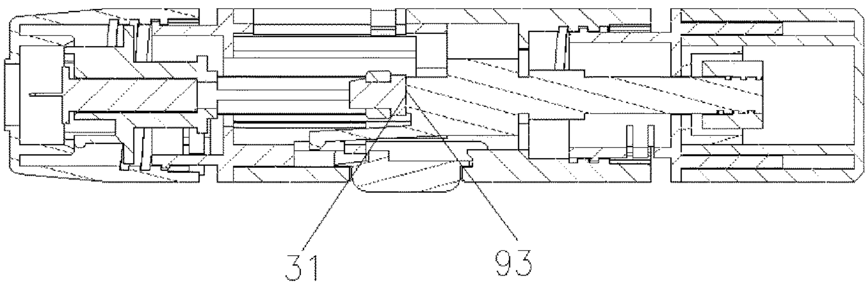
FIG. 17 exemplarily shows a schematic diagram of a trigger process, wherein the puncture distance and the elastic force are in the minimum state.
Figure 18:
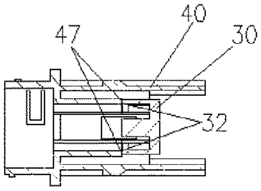
FIG. 18 exemplarily shows the cooperation of the guide sleeve and the stop block during the puncture of the needle tip.
Figure 19:
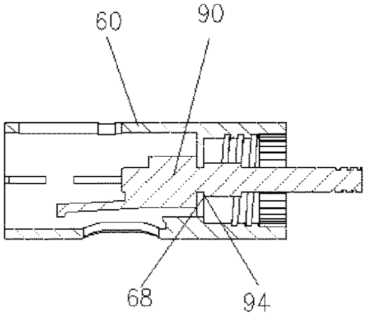
FIG. 19 exemplarily shows the cooperation of the driving core and the body during a trigger process.

During blood collection, the blood taking needle 50 is installed and fixed in the needle seat groove 21 through the needle outlet hole 11, the tail cap is pulled to drive the driving core 90 to axially move to depart from the needle outlet hole 11, until the elastic arm 91 slides over a second positioning surface 46, a first top face 92 abuts against the second positioning surface 46, the spring 150 is compressed by a fifth positioning surface 95, and the lancet device enters a state to be triggered (referring to FIG. 15-1); and the button 70 is pressed, the contact point 73 is in contact with a protrusion 98 to deform the elastic arm 91, the first top face 92 deviates from the control of the second positioning surface 46, so that the limitation to the driving core 90 is removed, the elastic force released from the compressed state of the spring 150 drives the driving core 90 to move instantly toward the direction of the needle outlet hole 11, until a third stop surface 94 hits a matching surface 68. Before the driving core 90 stops moving, a second top face 93 has hit a transmission surface 31 (referring to FIG. 17), the impact force drives the needle seat 20 to move, a needle tip portion 51 of the blood taking needle is exposed from a needle outlet, when a first stop surface 32 hits a second stop surface 47 (referring to FIG. 18), the needle seat 20 stops moving toward the direction of the needle outlet hole, and under the promotion of the spring 140, the needle tip of the blood taking needle retracts into the lancet device to complete the blood collection. The stop block 30 can be made of a soft rubber material to reduce the vibration during the impact.

Figures 1, 16:
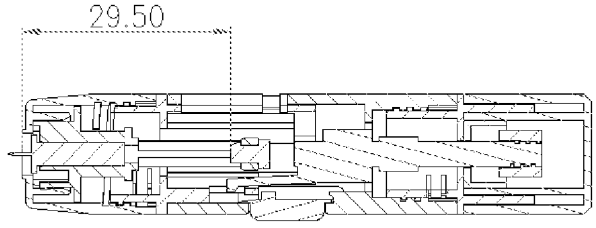
Figures 2, 16:
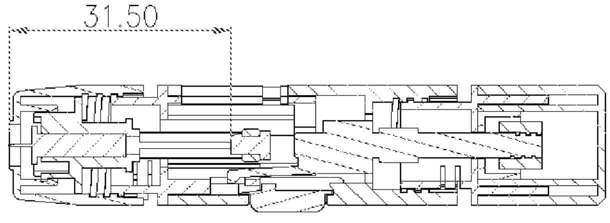
Figure 20:
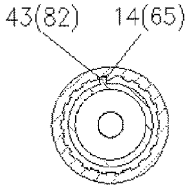
FIG. 20 exemplarily shows the cooperation of a hook and a blocking surface.

Preparatory works that can be made before blood collection include: 1. the puncture length of the blood taking needle is adjusted: the cap is rotated, because during a trigger process, the needle seat 20 will stop moving toward the direction of the needle outlet hole at the arrival of a specified position, the puncture length of the needle tip of the blood taking needle can be adjusted by the axial movement of the cap (referring to FIG. 16-1 and FIG. 16-2). 2. The elastic force when the spring 150 is triggered is adjusted: when the tail cap 110 is rotated, since the compression of the spring 150 is limited by the fifth positioning surface 95 and the separation piece 86 (referring to FIG. 15-1 and FIG. 15-2), the second thread rib 81 of the tail cap core 80 is driven by the positioning rib 111 to rotate along the second thread groove 64, in this case, when the fourth positioning surface 84 is in close contact with the rear end face 67, the tail cap core 80 is located at the nearest end, the compression amount of the spring is the maximum, and the elastic force is the maximum (referring to FIG. 15-1); and when the tail cap core 80 is rotated until a second hook 82 is in contact with a second blocking surface 65 (referring to FIG. 20), the tail cap core 80 cannot move further toward the far end due to the limitation of the second blocking surface 65, at this time, the tail cap core is located at the furthest end, the distance between the fifth positioning surface 95 and the separation piece 86 is the maximum, the compression amount of the spring is the minimum, and the elastic force is the minimum (referring to FIG. 15-2). The user can adjust the punctuate length and strength between the minimum and the maximum to suit his own needs.

In the above embodiment of the present disclosure, since the compression of the spring 150 is limited by the fifth positioning surface 95 and the separation piece 86, when the tail cap 110 is rotated, the second thread rib 81 of the tail cap core 80 is driven by the positioning rib 111 to rotate along the second thread groove 64, in this case, when the fourth positioning surface 84 is in close contact with the rear end face 67, the tail cap core 80 is located at the nearest end, the compression amount of the spring is the maximum, and the elastic force is the maximum; and when the tail cap core 80 is rotated until the second hook 82 is in contact with the second blocking surface 65, the tail cap core 80 cannot move further toward the far end due to the limitation of the second blocking surface 65, at this time, the tail cap core is located at the furthest end, the distance between the fifth positioning surface 95 and the separation piece 86 is the maximum, the compression amount of the spring is the minimum, and the elastic force is the minimum.

In the embodiment of the present disclosure, a plurality of elastic pieces 23 are provided to the periphery of the needle seat groove 21, the needle seat 20 axially reciprocates in the cap 10 during the blood collection process, and the needle seat 20 moves smoothly via the deformation of the elastic pieces 23 (acting with the limiting rib 12), thereby reducing the jitter of the blood taking needle during the blood collection process and reducing the pain of the user.

In the embodiment of the present disclosure, the space formed by the limiting rib 12 and the housing of the cap 10 can accommodate a part of the spring 140 so as to limit the amount of circumferential swing of the spring 140, so that the jitter of the blood taking needle during the blood collection process can be reduced, and the pain of the user can be alleviated.

In the embodiment of the present disclosure, by using the stop block made of a soft material, the vibration during the impact of the driving core and the needle seat can be reduced, and the pain of the user can be alleviated.

In the embodiment of the present disclosure, although the needle seat and the driving core are two separate components, they can also be formed into one component, which is also within the protection scope of the present disclosure.

There can be many variations to the above-described embodiment. For example, in the case where it is not necessary to use the tail cap to locate the lancet device in a standby position to be triggered, the lancet device may not be provided with the tail cap, or the tail cap may be directly integrated with the body of the lancet device; and as another example, the stop block may be not provided, but the puncture depth of the blood taking needle is selected or controlled through the cooperation between the driving spring and a return spring, so as to eliminate the pain caused by the lancet device to the user due to vibration.

Based on the above description, the present disclosure proposes the following solutions:

1. A lancet device, including:

a body;

a head cap, wherein a first end of the head cap is provided with a needle outlet hole, and a second end of the head cap is connected to the first end of the body;

a needle seat and a blood taking needle, wherein the needle seat is provided in the body, the blood taking needle is provided to the needle seat, and the needle tip of the blood taking needle is adapted to extend out from the needle outlet hole;

a driving core, which is adapted to drive the needle seat to move toward the needle outlet hole; and a driving spring for providing a trigger elastic force for the driving core, wherein:

the first end of the needle seat is provided with elastic arms that are evenly distributed in the circumferential direction, and the elastic arms elastically abut against an inner wall of the head cap or an annular wall provided in the head cap.

2. The lancet device according to 1, wherein:

the lancet device further includes a return spring, and the return spring is adapted to abut against between the head cap and the needle seat to provide an elastic force for retracting the ejected blood taking needle into the head cap.

3. The lancet device according to 2, wherein:

the elastic arms elastically abut against the annular wall provided in the head cap in an elastic abutting manner, and a space adapted to accommodate the return spring is defined between the annular wall and the inner wall of the head cap.

4. The lancet device according to 3, wherein:

the surface of the needle seat abutting against the return spring is a plane, and the abutting end portion of the return spring and the plane form surface contact.

5. The lancet device according to 1, further including:

a stop block provided at the second end of the needle seat, and the stop block cooperates with a corresponding blocking surface in the lancet device to define the movement position of the needle seat toward the needle outlet hole.

6. The lancet device according to 5, wherein:

the stop block comprises an elastomer.

7. The lancet device according to 1-6, further including:

an elastic force adjustment unit for adjusting the axial distance between the two ends of the driving spring to adjust the magnitude of the trigger elastic force.

8. A lancet device, including:

a body, having a first end and a second end;

a head cap, wherein the first end of the head cap is provided with a needle outlet hole, and the second end of the head cap is connected to the first end of the body;

a tail cap, wherein the first end of the tail cap is connected to the second end of the body;

a needle core assembly, at least a part of which is axially guided and located in the body, wherein the needle core assembly includes a needle seat and a blood taking needle, the blood taking needle is provided to the needle seat, and the needle tip of the blood taking needle is adapted to extend out from the needle outlet hole;

a trigger assembly, having a driving core acting on the needle seat, wherein the driving core is adapted to drive the needle seat to move toward the needle outlet hole based on a trigger operation; and a driving spring for providing a trigger elastic force for the driving core, wherein:

the first end of the needle seat is provided with elastic arms that are evenly distributed in the circumferential direction, and the elastic arms elastically abut against an inner wall of the head cap or an annular wall provided in the head cap.

Although the embodiments of the present disclosure have been shown and described, it can be understood by those of ordinary skill in the art that, modifications can be made to these embodiments without departing from the principles and spirit of the present disclosure, and the scope of the present disclosure is defined by the appended claims and their equivalents.

What is claimed is:

1. A lancet device, comprising:

a body;

a head cap, wherein a first end of the head cap is provided with a needle outlet hole, and a second end of the head cap is connected to a first end of the body;

a needle seat, wherein the needle seat is provided in the body, a blood taking needle is adapted to be provided to the needle seat, and a needle tip of the blood taking needle is adapted to extend out from the needle outlet hole;

a driving core adapted to drive the needle seat to move toward the needle outlet hole; and a driving spring for providing a trigger elastic force for the driving core, wherein:

the needle seat is provided with elastic arms at a first end thereof close to the needle outlet hole, the elastic arms are evenly distributed in a circumferential direction and are provided to be radially outward, during the movement of the needle seat and the blood taking needle toward the needle outlet hole, the elastic arms elastically abut against an inner wall of the head cap or the annular wall provided in the head cap so as to reduce jitter of the blood taking needle during the blood collection process.

2. The lancet device according to claim 1, wherein:

the lancet device further comprises a return spring, and the return spring is adapted to abut against between the head cap and the needle seat to provide an elastic force for retracting the blood taking needle into the head cap.

3. The lancet device according to claim 2, wherein:

the elastic arms elastically abut against the annular wall provided in the head cap in an elastic abutting manner, and a space adapted to accommodate the return spring is defined between the annular wall and the inner wall of the head cap.

4. The lancet device according to claim 3, wherein:

a surface of the needle seat abutting against the return spring is a plane, and an abutting end portion of the return spring and the plane form surface contact.

5. The lancet device according to claim 1, further comprising:

a stop block provided at a second end of the needle seat, and the stop block cooperates with a corresponding blocking surface in the lancet device to define a movement position of the needle seat toward the needle outlet hole.

6. The lancet device according to claim 5, wherein:

the stop block comprises an elastomer.

7. The lancet device according to claim 1, further comprising:

an elastic force adjustment unit for adjusting the axial distance between two ends of the driving spring to adjust a magnitude of the trigger elastic force.

8. The lancet device according to claim 2, further comprising:

an elastic force adjustment unit for adjusting the axial distance between two ends of the driving spring to adjust a magnitude of the trigger elastic force.

9. The lancet device according to claim 3, further comprising:

an elastic force adjustment unit for adjusting the axial distance between two ends of the driving spring to adjust a magnitude of the trigger elastic force.

10. The lancet device according to claim 4, further comprising:

an elastic force adjustment unit for adjusting the axial distance between two ends of the driving spring to adjust a magnitude of the trigger elastic force.

11. The lancet device according to claim 5, further comprising:

an elastic force adjustment unit for adjusting the axial distance between two ends of the driving spring to adjust a magnitude of the trigger elastic force.

12. The lancet device according to claim 6, further comprising:

an elastic force adjustment unit for adjusting the axial distance between two ends of the driving spring to adjust a magnitude of the trigger elastic force.

13. A lancet device, comprising:

a body, having a first end and a second end;

a head cap, wherein a first end of the head cap is provided with a needle outlet hole, and a second end of the head cap is connected to the first end of the body; and wherein an annular wall in the head cap is provided around the needle outlet hole and extends from the needle outlet hole towards the second end;

a tail cap, wherein a first end of the tail cap is connected to the second end of the body;

a needle core assembly, at least a part of which is axially guided and located in the body, wherein the needle core assembly includes a needle seat, a blood taking needle is adapted to be provided to the needle seat, and a needle tip of the blood taking needle is adapted to extend out from the needle outlet hole;

a trigger assembly, having a driving core acting on the needle seat, wherein the driving core is adapted to drive the needle seat to move toward the needle outlet hole based on a trigger operation; and a driving spring for providing a trigger elastic force for the driving core, wherein:

the needle seat is provided with elastic arms at a first end thereof close to the needle outlet hole, the elastic arms are evenly distributed in a circumferential direction and are provided to be radially outward, during the movement of the needle seat and the blood taking needle toward the needle outlet hole, the elastic arms elastically abut against an inner wall of the head cap or the annular wall provided in the head cap so as to reduce jitter of the blood taking needle during the blood collection process.

* * * * *